United States Patent [19]

Alexander et al.

[11] 4,391,807

[45] Jul. 5, 1983

[54] 6-SUBSTITUTED TETRAHYDROIMIDAZO[2,1-a]PHTHALAZINES AND USE AS BRONCHODILATORS

[75] Inventors: Catherine A. Alexander, Indianapolis; Robert J. Cregge, Zionsville; Norton P. Peet, Indianapolis, all of Ind.

[73] Assignee: The Dow Chemical Company, Midland, Mich.

[21] Appl. No.: 397,301

[22] Filed: Jul. 12, 1982

[51] Int. Cl.$^3$ .................. A61K 31/535; A61K 31/50; C07D 487/04
[52] U.S. Cl. .................................. 424/248.4; 424/43; 424/250; 544/115; 544/234; 260/243.3
[58] Field of Search .............................. 544/115, 234; 260/243.3; 424/248.4, 250, 43

[56] References Cited

U.S. PATENT DOCUMENTS 3,704,300 11/1972 Hardtmann .......................... 424/250
3,711,481 1/1973 Hardtmann .......................... 424/250
3,887,566 6/1975 Rodway et al. ..................... 424/250

OTHER PUBLICATIONS

Derwent Abstract 83179w/51, Belgian Patent 829,522.

Primary Examiner—Robert W. Ramsuer
Attorney, Agent, or Firm—John J. Kolano; Gary D. Street; Raymond A. McDonald

[57] ABSTRACT

Substituted tetrahydroimidazo[2,1-a]phthalazine compounds such as 6-methylamino-7,8,9,10-tetrahydroimidazo[2,1-a]phthalazine are prepared by reacting a 6-halo-7,8,9,10-tetrahydroimidazo[1,2-a]phthalazine with an appropriate amine. The compounds are useful as bronchodilators.

5 Claims, No Drawings

6-SUBSTITUTED TETRAHYDROIMIDAZO[2,1-a]PHTHALAZINES AND USE AS BRONCHODILATORS

The present invention relates to tetrahydroimidazo[2,1-a]phthalazines having an amino substituent at the 6-position. More particularly, it relates to compounds having the following general formula:

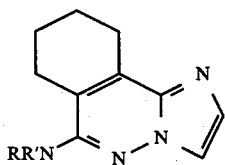

wherein —NRR' is (lower alkyl)amino, (lower alkyl)$_2$—amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl. The present invention further encompasses the pharmaceutically acceptable acid addition salts of the aforesaid amino compounds.

The lower alkyl groups referred to above contain 1 to 6 carbon atoms and can be exemplified by groups such as, methyl, ethyl, propyl, isopropyl, butyl, and hexyl.

Acid addition salts of the aforesaid compounds which pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicyclic, 4-aminosalicyclic, 2-phenoxybenzoic, 2-acetoxybenzoic, mandelic and like acids; and with organic sulfonic acids such as methanesulfonic acid and p-toluenesulfonic acid.

Examples of compounds encompassed by the present invention are the following:
6-Methylamino-7,8,9,10-tetrahydroimidazo[2,1-a]-phthalazine.
6-Dimethylamino-7,8,9,10-tetrahydroimidazo[2,1-a]phthalazine.
6-(Hexahydroazepin-1-yl)-7,8,9,10-tetrahydroimidazo[2,1-a]phthalazine.
6-(4-Methyl-1-piperazinyl)-7,8,9,10-tetrahydroimidazo[2,1-a]phthalazine.
6-(4-Methylhexahydro-1,4-diazepin-1yl)-7,8,9,10-tetrahydroimidazo[2,1-a]phthalazine.

The substituted tetrahydroimidazo[2,1-a]phthalazine compounds as described above are bronchodilators and are thus useful for the treatment of bronchial disorders such as bronchial asthma. The present invention is further directed to a method of effecting bronchodilation. Other testing has shown that the present compounds do not reduce blood pressure so that they are not hypotensives.

In practicing the method of this invention, an effective bronchodilating amount of 1 or more substituted tetrahydroimidazo[2,1-a]phthalazines of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 1 to about 100 milligrams of substituted tetrahydroimidazo[2,1-a]-phthalazine compound per kilogram of animal body weight with other ranges being from about 1 to about 10 or from 1 to about 3 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be fomulated in conventional time release capsule or tablet formulations although injectable compositions or sprays and aerosols for inhalation are preferred when rapid action is desired.

In practicing the method of this invention, the active ingredient is preferably incorporated in a composition comprising a pharmaceutical carrier and from about 5 to about 90 percent by weight of the substituted tetrahydroimidazo[2,1-]phthalazine compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

In evaluating bronchodilator activity, test compounds were administered to guinea pigs by intraperitoneal injection or orally and the guinea pigs were challenged by exposure to a histamine aerosol at periods ranging from 30 minutes to 4 hours later. Untreated animals collapsed when exposed to the histamine aerosol. In these operations, the animals were observed and collapse times were recorded. The collapse times observed were then compared statistically with control animals treated with water alone with the control group usually being a long-term cumulative control. When tested by the above procedure, the compounds of the present invention were found to produce a bronchodilating effect.

The compounds of the present invention are conveniently prepared by the reaction of a 6-halo-7,8,9,10-tetrahydroimidazo[2,1-a]phthalazine with an appropriate amine. The 6-halo substituent is preferably chlorine although it can also be bromine. This 6-halo compound is reacted with an excess of the amine in an inert solvent. More specifically, the reaction is carried out at the boiling temperature under reflux or at about 60° C. to 110° C. using an excess of the base or an inert organic solvent such as methanol, ethanol or 2-propanol as a medium. The product is recovered by conventional procedures such as concentration under reduced pressure.

The 6-chloro-7,8,9,10-tetrahydroimidazo[2,1-a]phthalazine used as the starting material is obtained by starting from 1,4-dichloro-5,6,7,8-tetrahydrophthalazine. This is reacted with an alkyl acetal of 2-aminoacetaldehyde, preferably the ethyl acetal, to replace one of the chlorines with a 2,2-diethoxyethylamino group. The resulting acetal is then treated with sulfuric acid to bring about cyclization and give the desired starting material referred to earlier.

The following examples are presented to illustrate the present invention but they should not be construed as limiting it in any way.

EXAMPLE 1

To 16.6 g of 2,2-diethoxyethylamine was added 5.1 g of 1,4-dichloro-5,6,7,8-tetrahydrophthalazine and the mixture was heated at reflux for 17 hours during which time the reaction turned brown. The excess starting material was removed by distillation to leave a tarry mixture which was heated at reflux in hexane. The resulting hexane solution was decanted, crystals formed in the decanted liquid, and the crystals were separated and purified by successive recrystallization from hexane. The product thus obtained was 4-chloro-1-(2,2-diethoxyethylamino)-5,6,7,8-tetrahydrophthalazine.

EXAMPLE 2

A solution was prepared by adding 10 g of 4-chloro-1-(2,2-diethoxyethylamino)-5,6,7,8-tetrahydro phthalazine to 50 ml of concentrated sulfuric acid and the solution was stirred at room temperature for 30 minutes. The mixture was then placed in an ice bath and made basic (pH of 8) by the addition of aqueous 50% sodiumhydroxide solution. The solid which formed was separated by filtration and then dissolved in water. The aqueous solution was extracted with methylene chloride several times and the combined extracts were evaporated to dryness at reduced pressure. The solid obtained in this way was 6-chloro-7,8,9,10-tetrahydroimidazo[2,1-a]phthalazine.

EXAMPLE 3

A mixture was prepared by adding 4.5 g of 6-chloro-7,8,9,10-tetrahydroimidazo[2,1-a]phthalazine to 8.7 g of pyrrolidine and this was heated at reflux for 6.5 hours during which time the mixture turned brown. The reaction mixture was then poured into about 150 ml of ice water. A solid formed immediately and this was separated by filtration and air dried to give 6-(1-pyrrolidinyl)-7,8,9,10-tetrahydroimidazo[2,1-a]phthalazine melting at about 128° C.

EXAMPLE 4

A mixture was prepared by adding 15 g of 6-chloro-7,8,9,10-tetrahydroimidazo[2,1-a]phthalazine to 30.5 g of piperidine and the mixture was heated at reflux for 72 hours. The mixture was subjected to preparative liquid chromatography using 15% acetone in methylene chloride to separate the desired product from the impurities. The appropriate fractions from the chromatography were combined and the solvent was evaporated under reduced pressure. The resulting solid was collected by filtration and dried to give 6-(1-piperidinyl)-7,8,9,10-tetrahydroimidazo[2,1-a]phthalazine melting at about 95° C. This compound has the following structural formula

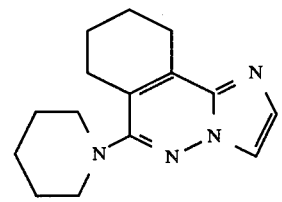

EXAMPLE 5

A mixture of 15 g of 6-chloro-7,8,9,10-tetrahydroimidazo[2,1-a]phthalazine and 36.2 g of 1-methylpiperazine was heated at reflux for 48 hours during which time the reaction mixture turned brown. The reaction was poured into about 150 ml of ice water. The solid which formed was separated by filtration and air-dried to give 6-(4-methyl-1-piperazinyl)-7,8,9,10-tetrahydroimidazo[2,1-a]phthalazine melting at about 79.5° C.

EXAMPLE 6

A mixture was prepared by adding 12 g of 6-chloro-7,8,9,10-tetrahydroimidazo[2,1-a]phthalazine to 28.7 g of 4-methyl-1-piperidine and the mixture was heated at reflux for 100 hours. It was then cooled and poured into about 200 ml of diethyl ether. The resulting mixture was allowed to stand for 4 hours, crystals formed, and these were separated by filtration and air-dried. The solid was then recrystallized from a mixture of 2-propanol and water to give 6-(4-methyl-1-piperidinyl)-7,8,9,10-tetrahydroimidazo[2,1-a]phthalazine melting at about 95°-95.5° C.

EXAMPLE 7

A mixture of 10 g of 6-chloro-7,8,9,10-tetrahydroimidazo[2,1-a]phthalazine and 20.9 g of morpholine was heated at reflux for 72 hours. The mixture was then poured into about 200 ml of ice water and a solid formed immediately. This was separated by filtration and air-dried to give 6-(4-morpholinyl)-7,8,9,10-tetrahydroimidazo[2,1-a]phthalazine melting at about 160°-161° C. This compound has the following structural formula

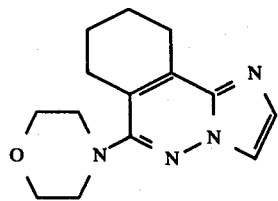

What is claimed is:
1. A compound of the formula:

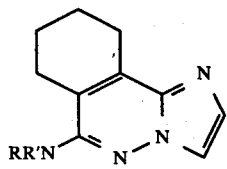

wherein —NRR' is (lower alkyl)amino, di(lower alkyl)amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl; and the pharmaceutically acceptable acid addition salts of said compound.

2. A compound according to claim 1 which is 6-(1-pyrrolindinyl)-7,8,9,10-tetrahydroimidazo[2,1-a]phthalazine.

3. A compound according to claim 1 which is 6-(4-methyl-1-piperazinyl)-7,8,9,10-tetrahydroimidazo[2,1-a]phthalazine.

4. A compound according to claim 1 which is 6-(4-morpholinyl)-7,8,9,10-tetrahydroimidazo[2,1-a]phthalazine.

5. A method of producing bronchodilation which comprises administering to a mammal in need thereof an effective amount of a compound of the formula

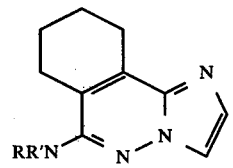

wherein —NRR' is (lower alkyl)amino, di(lower alkyl)amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl; and the pharmaceutically acceptable acid addition salts of said compound.

* * * * *